United States Patent
Wooster et al.

(10) Patent No.: US 9,649,275 B2
(45) Date of Patent: May 16, 2017

(54) NANOEMULSIONS

(75) Inventors: Timothy James Wooster, Hoppers Crossing (AU); Helen French Andrews, Mill Park (AU); Peerasak Sanguansri, Hoppers Crossing (AU)

(73) Assignee: COMMONWEALTH SCIENTIFIC AND INDUSTRIAL RESEARCH ORGANISATION, Campbell, ACT (AU)

( * ) Notice: Subject to any disclaimer, the term of this patent is extended or adjusted under 35 U.S.C. 154(b) by 1086 days.

(21) Appl. No.: 12/744,531

(22) PCT Filed: Nov. 18, 2008

(86) PCT No.: PCT/AU2008/001714
§ 371 (c)(1),
(2), (4) Date: Aug. 20, 2010

(87) PCT Pub. No.: WO2009/067734
PCT Pub. Date: Jun. 4, 2009

(65) Prior Publication Data
US 2010/0305218 A1  Dec. 2, 2010

(30) Foreign Application Priority Data
Nov. 28, 2007 (AU) .............................. 2007906504

(51) Int. Cl.
- *A61K 31/33* (2006.01)
- *A61K 9/107* (2006.01)
- *A61K 47/14* (2017.01)
- *A61K 47/44* (2017.01)

(52) U.S. Cl.
CPC ............ *A61K 9/1075* (2013.01); *A61K 47/14* (2013.01); *A61K 47/44* (2013.01)

(58) Field of Classification Search
CPC ....... A61K 9/1075; A61K 47/14; A61K 47/44
USPC .................................. 514/784; 426/238, 602
See application file for complete search history.

(56) References Cited

U.S. PATENT DOCUMENTS

| | | | |
|---|---|---|---|
| 5,698,219 A | 12/1997 | Valdivia et al. | |
| 5,753,241 A | 5/1998 | Ribier et al. | |
| 6,375,960 B1 | 4/2002 | Simonnet et al. | |
| 2002/0155084 A1* | 10/2002 | Roessler ............... | A61K 9/1075 424/70.21 |
| 2003/0087967 A1* | 5/2003 | Quemin ........................ | 514/772 |
| 2006/0233721 A1* | 10/2006 | Tamarkin et al. ............... | 424/47 |

FOREIGN PATENT DOCUMENTS

| | | | |
|---|---|---|---|
| CN | 1493289 A | | 5/2004 |
| CN | 1676125 A | | 10/2005 |
| CN | 1887270 A | | 1/2007 |
| EP | 0988585 | * | 3/2000 |
| JP | 01-288330 A | | 11/1980 |
| JP | 11-090211 A | | 4/1999 |
| JP | 2000-128733 A | | 5/2000 |
| WO | 2006/028339 A1 | | 3/2006 |
| WO | 2006028339 A1 | | 3/2006 |
| WO | 2006/087156 A1 | | 8/2006 |

OTHER PUBLICATIONS

Horaki et al, JP199-090211, published Apr. 6, 1999, Machine Translation used.*
Carole Chaix, et al; "Surface functionalization of oil-in-water nanoemulsion with a reactive copolymer: colloidal characterization and peptide immobilization", Colloids and Surfaces B: Biointerfaces, vol. 29, Issue 1, pp. 39-52, May 15, 2003.
International Search Report: PCT/AU2008/001714.
David Julian McClements; "Nanoemulsions versus microemulsions: terminolgy, differences, and similarities", Soft Matter, vol. 8, pp. 1719-1729; First published online Dec. 22, 2011.
Carole Chaix, et al; "Surface functionalization of oil-in-water nanoemulsion with a reactive copolymer: colloidal characterization and peptide immobilization", Colloids and Surfaces B: Biointerfaces 29, Issue 4, pp. 39-52, May 15, 2003.
Extended European Search Report dated Dec. 12, 2012. Appln. 08854541.3-2112/2222340 PCT/AU2008001714.
Zhu Shengshan (Editor); "New Pharmaceutical Dosage Forms", chemical Industry Press, 2003, paragraph 6, pp. 534.
Chinese Notice of Reexamination dated Jan. 23, 2017; Appln. No. 201310426059.2.

* cited by examiner

*Primary Examiner* — Jason Sims
*Assistant Examiner* — Ibrahim D Bori
(74) *Attorney, Agent, or Firm* — Ladas & Parry LLP (57) ABSTRACT

The present invention relates to oil-in-water nanoemulsions, processes for their preparation and their use as delivery vehicles for active components for use in opthalmological, dermatological, food, cosmetic, pharmaceutical, agrichemical, textile, polymer and chemical applications. The oil-in-water nanoemulsion comprises up to 40 volume % of an oil phase comprising at least 50 volume % of a triglyceride having a fatty acid chain length of 12 carbon atoms or greater and a hydrophilic non-ionic surfactant having a hydrophilic-lipophilic balance (HLB) greater than 7; and an aqueous phase, in which the oil droplets have an intensity average size of less than 100 nm and the ratio of surfactant to oil is less than 1:1, more preferably 0.2 to 0.8:1.

13 Claims, 5 Drawing Sheets

NANOEMULSIONS

FIELD

The present invention relates to oil-in-water nanoemulsions, processes for their preparation and their use as delivery vehicles for active components for use in opthalmological, dermatological, food, cosmetic, pharmaceutical, agrichemical, textile, polymer and chemical applications.

BACKGROUND

Emulsions are colloidal systems which have application in many industrial products such as food, cosmetics and pharmaceuticals. Oil-in-water emulsions are made of oil droplets which are dispersed in an aqueous continuous phase. One of the uses of emulsions in industry is to deliver active ingredients and components, such as, flavours, colours, vitamins, antioxidants, anti-microbials, pesticides, herbicides, cosmetics, nutraceuticals, phytochemicals and pharmaceuticals.

The active components can be oil soluble or water soluble, although their solubility in these environments can vary from highly soluble to poorly soluble. Administering active components that are not soluble in water poses a challenge as it requires the use of an appropriate vehicle for bringing an effective amount of the active component into the desired place of action. Oil-in-water emulsions are commonly used for the delivery of active components that are not soluble in water. Active components that are soluble in oil are dissolved/dispersed within the oil phase of the emulsion. Active components that are poorly soluble in both oil and water can be incorporated as part of the interfacial region of the oil-in-water emulsion.

The emulsions that are conventionally used to deliver active components suffer from a number of significant limitations and disadvantages. Emulsions are kinetically stable structures that are subject to destabilisation through a number of mechanisms, ultimately resulting in complete phase separation of the emulsion. The tendency of emulsions to physically alter over time presents problems for their storage and handling. Furthermore this physical degradation increases the likelihood that the preparation is in a suboptimal state when physically administered.

The size (diameter) of a conventional oil-in-water emulsion ranges from several hundred nanometers to several microns. Since these particles are in the order of or greater than the wavelength of light they have an opague appearance. This has the disadvantage of altering the optical clarity of any product that the emulsion is incorporated into, reducing visual appeal. Furthermore, emulsions of this size have a low interfacial area to volume ratio. This has a negative impact on the emulsions ability to dissolve poorly soluble bioactives which are soluble at an interface. The amount of a poorly soluble bioactive that can be dissolved at an interface being directly linked to the relative amount of interfacial area.

Another disadvantage of using conventional oil-in-water triglyceride emulsions to deliver active ingredients is that upon oral ingestion the release of the active ingredient is dependant on the rate and extent of lipolysis. Whilst such emulsions are capable of transporting active ingredients through the aqueous environment of the gastrointestinal tract, the ultimate release of the emulsified active ingredient is dependant on emulsion digestion. The rate of triglyceride emulsion digestion is a function of many factors, pH, co-lipase/lipase concentration, bile salt and emulsion surface area. Principle amongst them is the relative ratio of emulsion interfacial area to its volume. Emulsions with higher surface area to volume ratios undergo much faster lipolysis than those with low surface area to volume ratios.

When an emulsion has a particle size of less than 100 nm, the emulsion has the added benefit of becoming translucent or even transparent. The formation of very small (sub 100 nm) emulsions has the added benefit of increasing the relative amount of interfacial area considerably. An increase in the relative amount of interfacial area can lead to a greater ability to dissolve/disperse poorly soluble active components at the interface. Furthermore, an increase in the relative amount of interfacial area can lead to a faster rate of digestion by lipolysis compared to conventional oil-in-water emulsions. A faster rate of lipolysis can lead to a more rapid release of the emulsified active ingredient.

Two classes of emulsion that can have a particle size less than 100 nm are microemulsions or nanoemulsions. These two classes of emulsion are fundamentally different.

A microemulsion is an emulsion which forms spontaneously as a result of the ultralow interfacial tension and the favourable energy of structure formation. Microemulsions are thermodynamically stable having particle sizes that do not change with time. One disadvantage of a microemulsion is that it may become physically unstable if its composition is changed, e.g. upon dilution, acidification or heating. The spontaneous formation of a microemulsion arises from the synergistic interaction of surfactant, co-surfactant and co-solvent to effectively "solubilise" oil molecules. As a result it is known that a disadvantage of microemulsions is that they contain a high amount of surfactant relative to the amount of oil. In the case of foods, many surfactants have a bitter taste. Furthermore WHO and the FDA have placed restrictions on the daily intakes of many of these surfactants.

A nanoemulsion is an emulsion which does not form spontaneously, but is instead formed by the application of shear to a mixture of oil, water and surfactant. Unlike microemulsions, nanoemulsions are kinetically stable and their particle size may increase over time via coalescence, flocculation and/or Ostwald ripening. The very small size of nanoemulsions makes them particularly prone to particle size growth by Ostwald ripening. An increase in emulsion particle size over time is disadvantageous as the emulsion will lose its clarity accompanied with a corresponding increase surface area.

Like microemulsions, nanoemulsions can have the benefit of appearing translucent/transparent as a result of their small size. Also, like microemulsions, nanoemulsions have the benefit of having a high interfacial area to volume ratio which can aid in the dissolution of poorly soluble bioactives and aid the rapid digestion of the emulsion by faster rates of lipolysis. Furthermore, unlike many microemulsions, nanoemulsions retain their structure (small size) upon dilution and/or acidification. This may have the added benefit of aiding active adsorption as it is currently thought that emulsions below 100 nm have a greater ability to penetrate epithelial layers such as the skin and oral mucosa. Another advantage of nanoemulsions is that their creation requires the use of a significantly lower amount of surfactant compared to microemulsions. This gives the nanoemulsions the advantage that less surfactant is incorporated upon addition of a certain amount of active/oil. This is beneficial from a toxicological, regulatory and taste perspective.

The nature of the oil contained within the nanoemulsion is also important. It is advantageous to have an oil that is a triglyceride as they present a lower toxicological and/or irrigational profile to humans than synthetic or hydrocarbon oils. There are three classes of triglycerides, short chain triglycerides (less than 6 carbons in fatty acid chain), medium chain triglycerides (6 to 12 carbons in fatty acid chain) and long chain triglycerides (greater than 12 carbons in fatty acid chain). It is advantageous if the triglyceride oil within a nanoemulsion is of a long chain format, with preferably some degree of unsaturation as these oils have been shown to provide positive nutritional benefits and are considerably more stable against Ostwald ripening.

The creation of nanoemulsions and/or nanodispersions using medium chain triglycerides, especially miglyol 812, is known. Medium chain triglycerides are used as their smaller molecular bulk and higher solubility in water aids their ability to form nanoemulsions and/or nanodispersions. In contrast, it is known that the large molecular bulk of long chain triglycerides prevents them from readily forming clear microemulsions or nanoemulsions.

There remains the challenge of creating a nanoemulsion whose oil phase contains a long chain triglyceride where the emulsion has an intensity average size of less than 100 nm, high stability against Ostwald ripening and lower relative amounts of surfactant. The creation of such a nanoemulsion would be advantageous as it will increase product stability and clarity, improve the solubility of some poorly soluble actives and improve organoleptic properties.

SUMMARY

In a first aspect, there is provided an oil-in-water nanoemulsion which comprises
up to 40 volume % of an oil phase comprising at least 50 volume % of a triglyceride having a fatty acid chain length of 12 carbon atoms or greater;
a hydrophilic non-ionic surfactant having a hydrophilic-lipophilic balance (HLB) greater than 7; and
an aqueous phase,
in which the oil droplets of the nanoemulsion have an intensity average size of less than 100 nm and the ratio of surfactant to oil is less than 1:1, more preferably 0.2 to 0.8:1.

In a second aspect, there is provided a process for the preparation of an oil-in-water nanoemulsion which comprises
subjecting up to 40 volume % of an oil phase comprising at least 50 volume % of a triglyceride having a fatty acid chain length of 12 carbon atoms or greater and a hydrophilic non-ionic surfactant having a hydrophilic-lipophilic balance (HLB) greater than 7 and an aqueous phase to homogenisation, sonication or membrane emulsification to prepare a nanoemulsion in which the oil droplets have an intensity average size of less than 100 nm and the ratio of surfactant to oil is less than 1:1, more preferably 0.2 to 0.8:1.

In a third aspect, there is provided use of the nanoemulsion defined above as a delivery vehicle for active components.

The active components include ingredients and components for use in food, beverages, cosmetics, pharmaceutical, opthalmological, dermatological, agrichemical, textile, polymer and chemical applications.

There is also provided a delivery vehicle for active components comprising the nanoemulsion defined above.

In a fourth aspect, there is provided a formulation comprising the nanoemulsion defined above and an active component.

In a fifth aspect, there is provided a process for the preparation of the formulation defined above which comprises mixing the nanoemulsion defined above with the active component.

In a sixth aspect, there is provided a process for the preparation of the formulation defined above which comprises
subjecting the active component, up to 40 volume % of an oil phase comprising at least 50 volume % of a triglyceride having a fatty acid chain length of 12 carbon atoms or greater and a hydrophilic non-ionic surfactant having a hydrophilic-lipophilic balance (HLB) greater than 7 and an aqueous phase to homogenisation, sonication or membrane emulsification to prepare a nanoemulsion in which the oil particles have an intensity average size of less than 100 nm and the ratio of surfactant to oil is less than 1:1, more preferably 0.2 to 0.8:1.

DETAILED DESCRIPTION

The present invention relates to an oil-in-water nanoemulsion, a process of the preparation of the nanoemulsion and the use of the nanoemulsion for the delivery of active components.

The oil-in-water nanoemulsion comprises
up to 40 volume % of an oil phase comprising at least 50 volume % of a triglyceride having a fatty acid chain length of 12 carbon atoms or greater and a hydrophilic non-ionic surfactant having a hydrophilic-lipophilic balance (HLB) greater than 7; and
an aqueous phase,
in which the oil droplets have an intensity average size of less than 100 nm and the ratio of surfactant to oil is less than 1:1, more preferably 0.2 to 0.8:1.

In a preferred embodiment, the oil-in-water nanoemulsion comprises up to 40 volume % of an oil phase comprising at least 50 volume % of a triglyceride having a fatty acid chain length of 12 carbon atoms or greater, a hydrophilic non-ionic surfactant having a hydrophilic-lipophilic balance (HLB) greater than 7 and a co-solvent and an aqueous phase.

The nanoemulsion may also contain a co-surfactant which preferably interacts synergistically with the non-ionic surfactant to reduce emulsion particle size.

For food, cosmetics, pharmaceuticals, opthalmological and dermatogical applications, it is preferable that components are food grade or pharmaceutical grade thereby resulting in an edible nanoemulsion.

The nanoemulsions have high clarity, are physically stable against Ostwald ripening due to the use of long chain triglycerides and have good formulation stability as they can be readily diluted to infinitum. The lower surfactant to oil ratio also means that the nanoemulsions should have organoleptic appeal as surfactants are generally bitter in taste. The nanoemulsion is preferably food grade or pharmaceutical grade and the lower surfactant to oil ratio enables the incorporation of higher amounts of nanoemulsion into food products before breaching the regulatory level of synthetic surfactants in foods established by WHO and FDA.

Nanoemulsion

The term "nanoemulsion" refers to oil-in-water emulsions in which the oil droplets are ultra small having a diameter of 100 nm or less, preferably 80 nm or less, more preferably 75 nm or less, most preferably 60 nm or less. The droplet size is the Z-average or intensity weighted average size as measured by dynamic light scattering (also known as photon correlation spectroscopy).

Oil Phase

The oil phase comprises at least 50 volume % of a triglyceride having a fatty acid chain length of 12 carbon atoms or greater. The triglyceride can be a liquid or solid fat of animal, vegetable, algal or synthetic origin which is preferably food grade having the following general formula:

in which $R_1$, $R_2$ and $R_3$ are independently selected from saturated and unsaturated fatty acid residues (unbranched and branched) with chain lengths of $C_{12}$ or greater, preferably $C_{12}$-$C_{24}$, more preferably $C_{16}$-$C_{22}$, i.e. long chain triglycerides.

Figure 1:
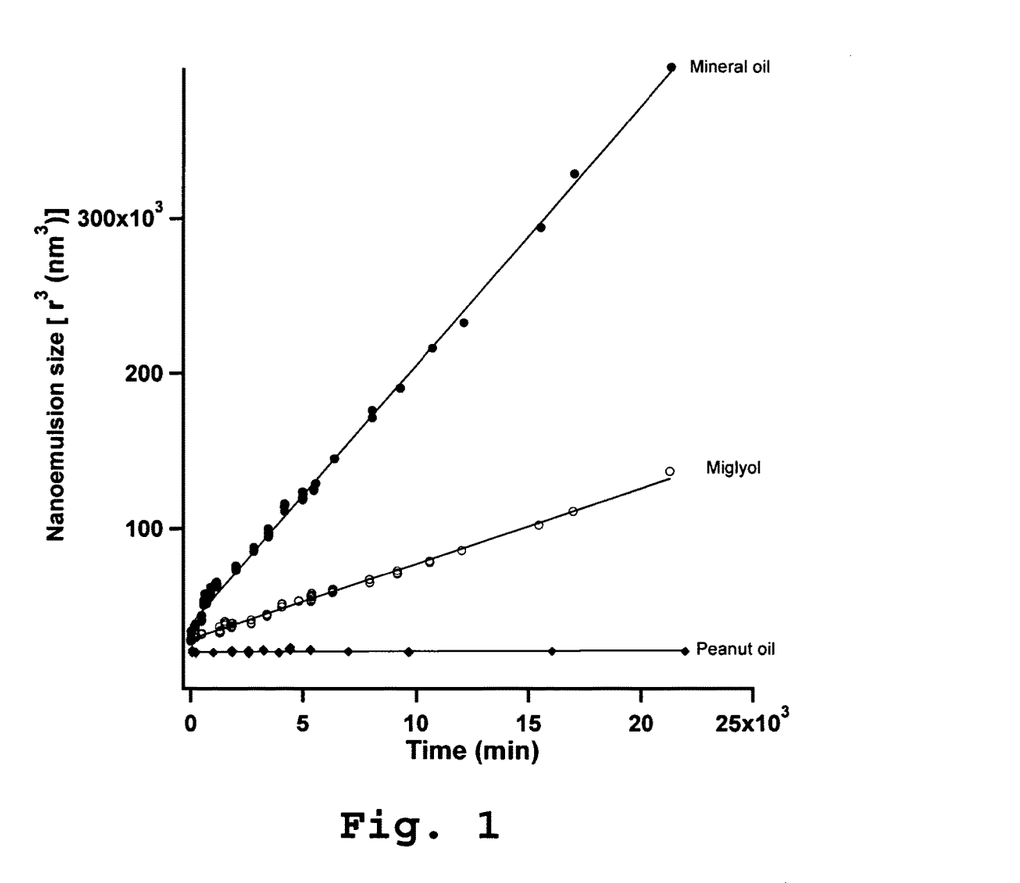
FIG. 1 is a graph comparing the change in nanoemulsion particle size over time for two triglyceride nanoemulsions made using i) a medium chain triglyceride (miglyol 812) and ii) a long chain triglyceride (peanut oil).
Figure 2:
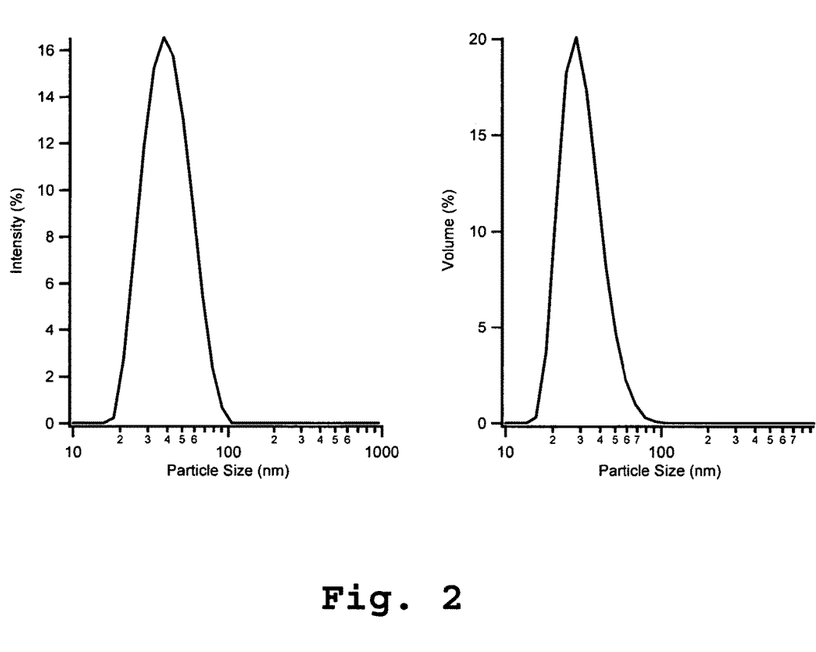
FIG. 2 are graphs describing the typical particle size distributions of nanoemulsions described in examples 2-6 as i) a intensity weighted particle size distribution ii) a volume weighted particle size distribution as measured by dynamic light scattering.

Long chain triglycerides, preferably having some degree of unsaturation have been shown to provide positive nutritional benefits and are considerably more stable against Ostwald ripening. FIG. 1 is a graph depicting the physical stability of nanoemulsions made using a mineral/paraffin oil (hexadecane), a medium chain triglyceride (miglyol 812) or a long chain triglyceride (peanut oil). The stability of the long chain triglyceride is evident from this graph.

Examples of long chain triglycerides include those of animal origin such as fish oil, cod liver oil, blubber, lard, tallow, schmaltz, and butter fat; vegetable origin such as canola oil, castor oil, cocoa butter, coconut oil, coffee seed oil, corn oil, cotton seed oil, evening primrose oil, grapeseed oil, flax seed oil, menhaden oil, mustard seed oil, olive oil, palm oil, palm kernel oil, peanut oil, poppy seed oil, rapeseed oil, rice bran oil, safflower oil, sesame oil, soybean oil, sunflower oil, palm kernel oil, hazelnut oil, sesame oil and wheat germ oil; algal origin such as vegetable oil Synthetic triglycerides, fractionated triglycerides, modified triglycerides, hydrogenated triglycerides or partially hydrogenated and mixtures of triglycerides are also included.

The nanoemulsion may contain one or more additional oils such as short chain triglycerides for example triacetin, tributyrin, tricapylrin and miglyol; mineral oils for example alkane oils such as decane, tetradecane, hexadecane and octadecane; and flavour oils for example limonene, mandarin oil orange oil, lemon oil, lime oil or other citrus oils, peppermint oil, peach oil, vanilla flavour oil and vanillin; and aromatic oils for example peppermint, tea tree oil, eucalyptus oil, mentha arvensis, cedarwood oil, spearmint, orange oil, lemin oil and clove.

The ratio of triglyceride to additional oil is preferably 1:0 to 1:1.

The total amount of oil in the nanoemulsion including long chain triglyceride and additional oil if present may be 0.01 to 70 wt %, preferably 0.01 to 50 wt %, more preferably 0.01 to 40 wt %.

Hydrophilic Non-Ionic Surfactant

The hydrophilic non-ionic surfactant has a hydrophilic-lipophilic balance (HLB) greater than 7 and is preferably a food grade or pharmaceutical grade hydrophilic surfactant such as polysorbates (polyethylene glycol sorbitan fatty acid esters), polyethylene glycol alkyl ethers, sugar esters, polyethoxylated fatty acids, polyoxyethylene-polyoxypropylene block co-polymers (Pluronics), polyethylene glycol alkyl phenol surfactants, citric acid esters of monoglycerides, polyglycerol esters, polyethoxylated fatty acid diesters, PEG-fatty acid mono and diesters, polyethylene glycol glycerol fatty acid esters and alcohol oil transesters or mixtures thereof.

Suitable non-ionic surfactants include:

polysorbates for example polyethoxyethylene sorbitan monoesters, including polyoxyethylene sorbitan monolaurate (Tween 20), polyoxyethylene sorbitan monopalmitate (Tween 40), polyoxyethylene sorbitan monostearate (Tween 60), polyoxyethylene sorbitan tristearate (Tween 65) and polyoxyethylene sorbitan mono-oleate (Tween 80);

sugar surfactants for example sucrose monopalmitate, sucrose monolaurate, sucrose distearate 3 Crodesta F-10, sucrose distearate, monostearate Crodesta F-110, sucrose dipalmitate, sucrose monostearate Crodesta F-160, sucrose monopalmitate, sucrose monolaurate and saccharose monolaurate;

polyoxyethylene-polyoxypropylene block co-polymers which are available under various trade names including Synperonic PE series (ICI), Pluronic® series (BASF), Emkalyx, Lutrol (BASF), Supronic, Monolan, Pluracare and Plurodac.

The polyoxyethylene-polyoxypropylene block co-polymers are also known as "polyoxamers" and have the general formula:

$$HO(C_2H_4O)_A(C_3H_6O)_B(C_2H_4O)_AH$$

in which A and B denote the number of polyoxyethylene and polyoxypropylene units, respectively.

Polyoxamers when A is 1-100 and B is 1-100 and combinations thereof are suitable for use in the nanoemulsions of the present invention.

The amount of hydrophilic surfactant in the nanoemulsion may be 0.1 to 15 wt %, preferably 1 to 10 wt %, more preferably 3 to 7 wt %.

Co-Surfactant

The nanoemulsion may also contain a co-surfactant which is preferably a surfactant that acts synergistically with the hydrophilic non-ionic surfactant to alter the interfacial curvature. This lowers interfacial tension, permitting easier emulsion formation.

Preferably the co-surfactant is food grade or pharmaceutical grade.

Suitable food grade co-surfactants include:

sorbitan fatty acid esters such as sorbitan monolaurate (Span 20), sorbitan monopalmitate (Span 40), sorbitan tristearate (Span 65), sorbitan monostearate (Span 60), sorbitan monooleate (Span-80) and sorbitan trioleate (Span-85);

phospholipids such as egg/soy lecithin for example epikuron, topcithin, leciprime, lecisoy, emulfluid, emulpur, metarin, emultop, lecigran, lecimulthin, ovothin lyso egg/soy lecithin, hydroxylated lecithin lysophosphatidylcholine, cardiolipin, sphingomyelin, phosphatidylcholine, phosphatidyl ethanolamine, phosphatidic acid, phosphatidyl glycerol, phosphatidyl serine and mixtures of phospholipids with other surfactants; and ionic surfactants such as sodium stearoyl lactylate and calcium stearoyl lactylate.

The amount of co-surfactant in the nanoemulsion may be 0.1 to 15 wt %. Preferably the co-surfactant is present in a ratio relative to the hydrophilic non-ionic surfactant of 0:1 to 2:1, more preferably 0:1 to 1.3:1 and most preferably 0.5:1 to 1.3:1.

Aqueous Phase

The aqueous phase can be either purified or ultrapure water, saline or buffered saline.

The balance of water after the inclusion of all other formulation components in the nanoemulsion may be 50 to 100 wt %, preferably 40 to 99.99 wt %, more preferably 30 to 99.90 wt %.

Co-Solvent

In a preferred embodiment, the nanoemulsion also contains a co-solvent. The co-solvent lowers the interfacial tension of the aqueous phase which thereby enables the formation of smaller emulsion droplet sizes.

Suitable co-solvents include $C_1$-$C_{10}$ alcohols such as methanol, ethanol, propanol, butanol, pentanol, hexanol, heptanol, octanol, nonanol and decanol; polyols such as glycerol, 1,2 propandiol, 1,3 propandiol, polyethylene glycol and polypropylene glycol; and long chain fatty alcohols. Preferably, the solvent is a $C_1$-$C_4$ alcohol, more preferably ethanol.

The amount of solvent in the nanoemulsion may be 0 to 70 wt %, preferably 0 to 50 wt %, more preferably 15 to 45 wt %.

Active Component

The active component is any component that is an oil, oil-soluble, partitions to an oil phase, poorly soluble in oil and water or soluble or capable of being dispersed at an interface which imparts either a colour, aroma, flavour, antimicrobial effect, beautification effect, health promoting effect, disease prevention effect or technique, or disease curing effect to the nanoemulsion.

The active components may be food or beverage ingredients such as food supplements, food additives, aromas, aromatic oils, colours, flavours and sweeteners; cosmetics; pharmaceuticals such as medicaments, peptides, proteins and carbohydrates; nutraceuticals; phytochemicals; vitamins; essential polyunsaturated fatty acids; plant extracts; agrichemicals such as pestides and herbicides; textiles; polymers; and chemicals.

Suitable active components include:

phytochemicals such as polyphenols (e.g., catechin, epicatechin, epicatechin gallate, quercitin and resveratrol), carotenoids (e.g., lycopene, lutein, lutein esters, β-carotene, retinyl, retinyl palmitate and zeaxanthin), ubiquinone (CoQ10) and phytosterols;

vitamins such as vitamin A (e.g., retinol and retinol palmitate), Vitamin D (e.g., calciferol), vitamin E (e.g., tocopherol, tocopherol acetate and tocopherol palmitate), vitamin K (e.g., $K_1$—phylloquinone and $K_2$—menaquinone)

essential polyunsaturated fatty acids such as linoleic acid, alpha-linolenic acid, eicosapentaenoic acid and docosahexaenoic acid;

flavours such as natural flavour oils for example citrus oil, limonene, mandarin oil orange oil, lemon oil, lime oil, peppermint oil, peach oil, vanilla flavour oil and vanillin or synthetic flavoring materials for example hexyl alcohol, ethyl laurate, apple flavoring oil, strawberry flavoring oil, benzaldehyde, cinnamic aldehyde, paprica flavoring oil, citronellyl butyrate, phenyl ethyl acetate, ethyl propionate, ethyl decanoate, ethyl butyrate, ethyl hexanoate, brandy flavoring oil, hexyl aldehyde, blackberry flavoring oil, phelandrene, blueberry flavoring oil, honey flavoring, oil, nerol, licorice flavoring oil, maple flavoring oil, ethyl caprylate and watermelon flavoring oil; and aromatic oils such as peppermint, tea tree oil, eucalyptus oil, mentha arvensis, cedarwood oil, spearmint, orange oil lemin oil and clove.

The amount of active component in the nanoemulsion may be 0.01 to 50 preferably 0.01 to 10 wt %.

Additives

The nanoemulsion may contain additives such as stabilisers, antioxidants, preservatives, buffering agents, charge inducing agents, weighting agents polymers and proteins. Stabilisers can be pH modifying agents, anti-creaming or anti-foaming agents or agents which impart stability to the nanoemulsion. Examples of stabilisers include sodium oleate, glycerine, xylitol, sorbitol, ascorbic acid, citric acid and sodium edetate. Antioxidants include carotenoids, for example alpha-tocopherol or its derivatives, which are members of the Vitamin E family, β-carotene, lutein, lycopene, ascorbic acid, trolox, β-carotene, polyphenols such as catechin, epicatechin, epicatechin gallate, quercetin, resveratrol, ascorbyl palmitate and butylated hydroxytoluene (BHT). Buffering agents include sodium phosphate, citric acid, formic acid and ascorbic acid. Examples of charge inducing agents include sodium deoxycholate, sodium lauryl sulfate, deoxycholic acid, stearylamine, oleylamine, chitosan and cetyltriethylammonium bromide. Weighting agents include brominated vegetable oils. Examples of polymers and proteins include hydrocolloids such as guar gum, pectin, xanthan and alginate.

The amount of additive in the nanoemulsion may be 0 to 50 wt %, preferably 0 to 25 wt %, more preferably 0 to 10 wt %.

Process

The process for preparing nanoemulsion in its broadest sense includes subjecting the oil phase comprising the triglyceride, hydrophilic surfactant, aqueous phase and the co-solvent and/or co-surfactant when present to homogenisation, sonication or membrane emulsification, preferably high shear homogenisation. The interaction between the hydrophilic surfactant and the co-solvent and/or the co-surfactant when present reduces the interfacial tension of the emulsion which leads to better homogenisation and a smaller nanoemulsion particle size. The homogenisation can be performed using any suitable known homogenisation apparatus such as a microfluidiser (such as Microfluidics M-110Y Microfluidiser made by MFIC Corporation), high pressure homogeniser (such as one made by Gauline, Avestin or Niro Soavi the like) or a probe sonicator at pressures such as 1000 bar. Examples of apparatus which can be used for sonication include Hielscher ultrasonic homogenisers, Branson ultrasonic homogenisers, Cole-Palmer ultrasonic homogenisers or Omni Ruptor 4000 ultrasonic homogenisers. The membrane emulsification can be performed using for example a Polytron PT 3100 membrane homogeniser or a LiposoFast membrane homogeniser (Avestin, Canada). The number of passes through the homogenisation apparatus can vary depending on the desired particle size of the nanoemulsions, usually 5 passes will suffice.

In one embodiment, the nanoemulsion can be prepared by adding the hydrophilic surfactant and the co-surfactant to the oil phase comprising triglyceride and additional oil if present. Preferably the triglyceride oil and the additional oil are premixed. The oil/surfactant combination is then mixed with a solution containing the aqueous phase and the co-solvent using any suitable known mixing apparatus such as a Silverson rotor stator mixer at 12,000 rpm for about 2 minutes to form a pre-emulsion. The pre-emulsion is then subjected to homogenisation.

The formulation can be prepared by mixing the nanoemulsion with the active component, preferably by stirring at room temperature for a suitable period of time such as 12 hours at room temperature or several hours at elevated temperatures for example 60° C. In another embodiment, the formulation can be prepared by mixing the active component with the components of the emulsion and the resulting mixture is then homogenised. The final formulation is generally clear which indicates that the nanoemulsion has dissolved/incorporated the active component.

Formulation

The nanoemulsion can function as a delivery vehicle for active components which may be soluble in oil, partition to an oil phase or are poorly soluble in both oil and water. The active components can be entrapped in the nanoemulsion and incorporated into a formulation maintaining its stability.

It will be appreciated by those skilled in the art that is it most preferable to prepare the nanoemulsion as a concentrate, preferably with an oil content of 15 to 40 vol %. The same nanoemulsions can also be prepared at much lower oil contents, e.g. 0.1 to 10 vol %. Whilst it is preferable for the nanoemulsion to be prepared as a concentrate, it is also preferable to add the nanoemulsion to a food product in a diluted form ranging from 0.01 to 30 vol %.

EXAMPLES

The invention will now be described with reference to the following non-limiting examples.

Processing Conditions

A triglyceride oil nanoemulsion was prepared by creating a pre-emulsion of a mixture of ingredients as outlined in the below examples using a silverson rotor stator mixer at 12,000 rpm for 2 minutes. Nanoemulsions were prepared from pre-emulsions using a Microfluidics M-110Y microfluidizer (MFIC Corporation, Newton, Mass., USA) with a F20 Y 75 μm interaction chamber and H30 Z 200 μm auxiliary chamber inline. Transparent nanoemulsions were prepared by subjecting pre-emulsions to 5 passes (unless otherwise stated) at 1000 bar.

Formulation Examples

The examples of formulations set out below have several factors that contribute to the small emulsion size. It is an interaction between the oil (or a mixture of oils), a hydrophilic surfactant, a co-solvent and a co-surfactant that creates a favourably low interfacial tension that enables the reduction of the emulsion particle size to around 50-60 nm.

The main formulation is a triglyceride oil with a side chain length equal to or greater than 12 carbons, polyoxyethylene sorbitan mono ester (Tween) as the hydrophilic surfactant and ethanol as the co-solvent. Different types of nanoemulsion arise from the different co-surfactants used these include: various lecithins, sorbitan monoester surfactants (Span) and sodium stearoyl lactylate and many like co-surfactants.

All of the formulation examples have been found to work equally well with any of the triglyceride oils.

Example 1

A Peanut Oil Nanoemulsion-Tween/Ethanol

A peanut oil in water nanoemulsion was prepared by adding 12 grams of polyoxyethylene sorbitan mono-oleate (Tween 80) to 23 grams of peanut oil. This oil/surfactant mixture was then intermixed into 120 g of a 3 to 2 water to ethanol solution with a Silverson rotor stator mixer at 12,000 rpm for 2 minutes to form a pre-emulsion. The pre-emulsion was then homogenised with a Microfluidizer™ at 1000 bar and 5 passes. The resulting nanoemulsion had a particle size of 45 nm, and high optical clarity. If diluted with water (10 to 99% dilution) the nanoemulsion exhibited no change in size over a 100 day storage period.

Oil content: If the ratio of Tween 80 to oil are kept the same this formulation will work up to an oil content of 25-30%.

This formulation will work equally well with the following substitutions:

Polyoxyethylene surfactant: Tween 40 and Tween 60. Tween contents ranging from 6 g to greater than 30 g.

Ethanol content: an aqueous phase ethanol content ranging from 20 to 50%.

Fat/Oil: Lard, butter fat, canola oil, rapeseed oil, fish oil, sunflower oil, flax seed oil, safflower oil, palm oil, coconut oil, soybean oil, olive oil, corn oil, or any other tri-glyceride oil or combinations thereof.

Example 2

A Flax Seed Oil Nanoemulsion—Tween/Ethanol/Emultop IP

A flax seed oil nanoemulsion was prepared by adding 8 grams of polyoxyethylene sorbitan mono-oleate (Tween 80) and 5 grams of Emultop IP (lysolecithin) to 22.5 grams of flax seed oil. This oil/surfactant mixture was then intermixed into 120 g of a 3 to 1 water to ethanol solution with a silverson rotor stator mixer at 12,000 rpm for 2 minutes to form a pre-emulsion. The pre-emulsion was then homogenised with a microfluidiser at 1000 bar and 5 passes. The resulting nanoemulsion had a particle size of 45 nm, had high optical clarity and did not change size or optical clarity over a 100 day storage period.

Oil content: If the ratio of between 80 and co-surfactant to oil are kept the same this formulation will work up to an oil content of 25-30%.

This formulation will work equally well with the following substitutions:

Polyoxyethylene surfactant: Tween 40 and Tween 60. Tween contents ranging from 6 g up to 30 g.

Ethanol content: an aqueous phase ethanol content ranging from 20 to 50%.

Fat/Oil: Lard, butter fat, canola oil, rapeseed oil, fish oil, sunflower oil, peanut oil, safflower oil, palm oil, coconut oil, soybean oil, olive oil, corn oil, or any other tri-glyceride oil or combinations thereof.

Example 3

A Tuna Oil Nanoemulsion—Tween/Ethanol/Centromix E

A tuna oil nanoemulsion was prepared by adding 8 grams of polyoxyethylene sorbitan mono-oleate (Tween 80) and 8 grams of Centromix E (lysolecithin) to 22.5 grams of tuna oil. This oil/surfactant mixture was then intermixed into 120 g of a 3 to 1 water to ethanol solution with a silverson rotor stator mixer at 12,000 rpm for 2 minutes to form a pre-emulsion. The pre-emulsion was then homogenised with a microfluidiser at 1000 bar and 5 passes. The resulting nanoemulsion had a particle size of 45 nm, had high optical clarity and did not change size or optical clarity over a 100 day storage period.

Oil content: If the ratio of Tween 80 and co-surfactant to oil are kept the same this formulation will work up to an oil content of 25-30%.

This formulation will work equally well with the following substitutions:

Polyoxyethylene surfactant: Tween 40 and Tween 60. Tween contents ranging from 6 g up to 30 g.

Ethanol content: an aqueous phase ethanol content ranging from 20 to 50%.

Oil: Canola oil, rapeseed oil, fish oil, sunflower oil, peanut oil and flax seed oil.

Example 4

A Peanut Oil Nanoemulsion—Tween/Ethanol/Span 80

A peanut oil nanoemulsion was prepared by adding 8 grams of polyoxyethylene sorbitan mono-oleate (Tween 80) and 6 grams of sorbitan mono-oleate (Span 80) to 22.5 grams of peanut oil. This oil/surfactant mixture was then intermixed into 120 g of a 3 to 1 water to ethanol solution with a silverson rotor stator mixer at 12,000 rpm for 2 minutes to form a pre-emulsion. The pre-emulsion was then homogenised with a microfluidiser at 1000 bar and 5 passes. The resulting nanoemulsion had a particle size of 45 nm, had high optical clarity and did not change size or optical clarity over a 100 day storage period.

Oil content: If the ratio of between 80 and co-surfactant to oil are kept the same this formulation will work up to an oil content of 25-30%.

This formulation will work equally well with the following substitutions:

Polyoxyethylene surfactant: Tween 40 and Tween 60. Tween contents ranging from 6 g up to 30 g.

Ethanol content: an aqueous phase ethanol content ranging from 20 to 50%.

Oil: Canola oil, rapeseed oil, fish oil, sunflower oil and flax seed oil

Example 5

A Canola Oil Nanoemulsion—Tween/Ethanol/Sodium Steroyl Lactylate

A canola oil nanoemulsion was prepared by adding 8 grams of polyoxyethylene sorbitan mono-oleate (Tween 80) and 5 grams of sodium stearoyl lactylate (SSL) to 22.5 grams of canola oil. This oil/surfactant mixture was then intermixed into 120 g of a 3 to 1 water to ethanol solution with a silverson rotor stator mixer at 12,000 rpm for 2 minutes to form a pre-emulsion. The pre-emulsion was then homogenised with a microfluidiser at 1000 bar and 5 passes. The resulting nanoemulsion had a particle size of 45 nm, had high optical clarity and did not change size or optical clarity over a 100 day storage period.

Oil content: If the ratio of between 80 and co-surfactant to oil are kept the same this formulation will work up to an oil content of 25-30%.

This formulation will work equally well with the following substitutions:

Polyoxyethylene surfactant: Tween 40, Tween 60 and Tween 80, Tween contents ranging from 6 g up to 30 g.

Ethanol content: an aqueous phase ethanol content ranging from 20 to 50%.

Oil: Rapeseed oil, fish oil, sunflower oil, peanut oil and flax seed oil.

Example 6

A Mixed Oil Nanoemulsion—Tween/Ethanol/Lecithin

A mixed triglyceride oil nanoemulsion was prepared by adding 8 grams of polyoxyethylene sorbitan mono-oleate (Tween 80) and 8 grams of Centromix E (lysolecithin) to 22 g of a 50:50 mixture of peanut oil and miglyol that had been thoroughly premixed. This oil/surfactant mixture was then intermixed into 120 g of a 3 to 1 water to ethanol solution with a silverson rotor stator mixer at 12,000 rpm for 2 minutes to form a pre-emulsion. The pre-emulsion was then homogenised with a microfluidiser at 1000 bar and 5 passes. The resulting nanoemulsion had a particle size of 45 nm, had high optical clarity and did not change size or optical clarity over a 100 day storage period.

This formulation will work equally well with the following substitutions:

Polyoxyethylene surfactant: Tween 40, Tween 60 and Tween 80.

Oil: Canola oil, rapeseed oil, fish oil, sunflower oil and flax seed oil.

Ethanol content: an aqueous phase ethanol content ranging from 20 to 50%.

Substitutions: The additional oil, miglyol can be substituted with any mutually miscible oil including: tributyrn, tricapylrin, triacetin, limonene, orange oil, lemon oil, decane, tetradecane and hexadecane.

Example 7

Flavour Oil Nanoemulsion Example a Clear Orange Oil Flavour Concentrate

An orange flavour oil nanoemulsion was prepared by first thoroughly mixing 9 g of orange oil with 11.5 grams of peanut oil. To this mixture of orange oil/peanut oil 8 grams of polyoxyethylene sorbitan mono-oleate (Tween 80) and 5 grams of Emultop IP (lysolecithin) were added. This oil/emulsifier mixture was then intermixed into 120 g of a 3 to 1 water to ethanol solution with a silverson rotor stator mixer at 12,000 rpm for 2 minutes to form a pre-emulsion. The pre-emulsion was then homogenised with a microfluidiser at 1000 bar and 5 passes. The resulting orange flavour nanoemulsion had a particle size of 45 nm and had high optical clarity. This orange flavour oil nanoemulsion was added to sparkling water at 0.01 wt % to create an orange flavoured sparking water.

Comparative Examples

TABLE 1

Summary of size, clarity and physical stability of dispersions made formulations using a medium chain triglyceride miglyol

| Example | Oil core | Size | High clarity | Stable | Dilutable with water (clarity maintained with dilution) |
|---|---|---|---|---|---|
| 8 - nano-dispersion | Miglyol 812 | <40 nm | yes | No | no |
| 9 - nanoemulsion | Miglyol 812 | 45 nm | yes | No | yes |
| 10 - nanoemulsion | Miglyol 812 | 60 nm | yes | No | yes |

Comparative Example 8

Medium Chain Triglyceride Oil-in-Water Water Nanodispersions

| | |
|---|---|
| Soybean lecithin | 17.3% |
| Polysorbate 80 | 34.0% |
| Miglyol 812 | 34.5% |
| ethanol | 14.2% |

Preparation:
Part A—Nanodispersion:

Miglyol 812 and polysorbate 80 were mixed. The soybean lecithin was dissolved in ethanol and added to this mixture with stirring from a magnetic stirring mantle. The resulting solution was a clear homogeneous liquid, indicating the formation of nanodispersion.

Part B—Dilution with Water:

Dilution of this solution with water at 50° C., to an oil content of 10%, lead to the formation of a turbid white dispersion that had an average particle size of 2 micrometers, indicating the formation of a conventionally sized emulsion.

Comparative Example 9

Medium Chain Triglyceride Nanoemulsion

A medium chain triglyceride nanoemulsion was prepared by adding 8 grams of polyoxyethylene sorbitan mono-ester (Tween 80) and 8 grams of Centromix E (lysolecithin) to 22 g of miglyol 812 that had been thoroughly premixed. This oil/surfactant mixture was then intermixed into 120 g of a 3 to 1 water to ethanol solution with a silverson rotor stator mixer at 12,000 rpm for 2 minutes to form a pre-emulsion. The pre-emulsion was then homogenised with a Microfluidizer™ at 1000 bar and 5 passes. The resulting nanoemulsion had an initial particle size of 45 nm and initially had high optical clarity. However, this nanoemulsion was unstable to Ostwald ripening and its size increased over several weeks to the point where the nanoemulsion lost clarity, refer to FIG. 1.

Comparative Example 10

Medium Chain Triglyceride Nanoemulsion Using Tween 80

A medium chain triglyceride nanoemulsion was prepared by adding 24 grams of polyoxyethylene sorbitan mono-ester (Tween 80) to 23.5 g of miglyol 812. This oil/surfactant mixture was then intermixed into 120 g of water with a silverson rotor stator mixer at 12,000 rpm for 2 minutes to form a pre-emulsion. The pre-emulsion was then homogenised with a Microfluidizer™ at 1000 bar and 5 passes. The resulting dispersion had a transparent bluish colour and a particle size of 60 nm indicating the formation of a high clarity nanoemulsion of a medium chain triglyceride. However, this nanoemulsion was unstable to Ostwald ripening and its size increased over several weeks to the point where the nanoemulsion lost clarity over four weeks.

Bioactive Delivery Examples

Example 11

Resveratrol Nanoemulsion

A nutritional supplement was created by intermixing powdered resveratrol with a clear triglyceride nanoemulsion. Briefly, 300 mg of high purity resveratrol was intermixed with 100 ml of a nanoemulsion formulated according to any of examples 1-3 by stirring at room temperature for 4 hours. The resulting solution was clear and there way no indication of insoluble resveratrol particles, indicating that the nanoemulsion had dissolved the resveratrol.

This formulation will work equally well with the following substitutions:

The resveratrol is added to the emulsion ingredient mixture, as a solid powder or dissolved/dispersed in one of the ingredients, either prior to pre-emulsion formation or just prior to microfluidization.

Example 12

Phytosterol Nanoemulsion

Figure 3:
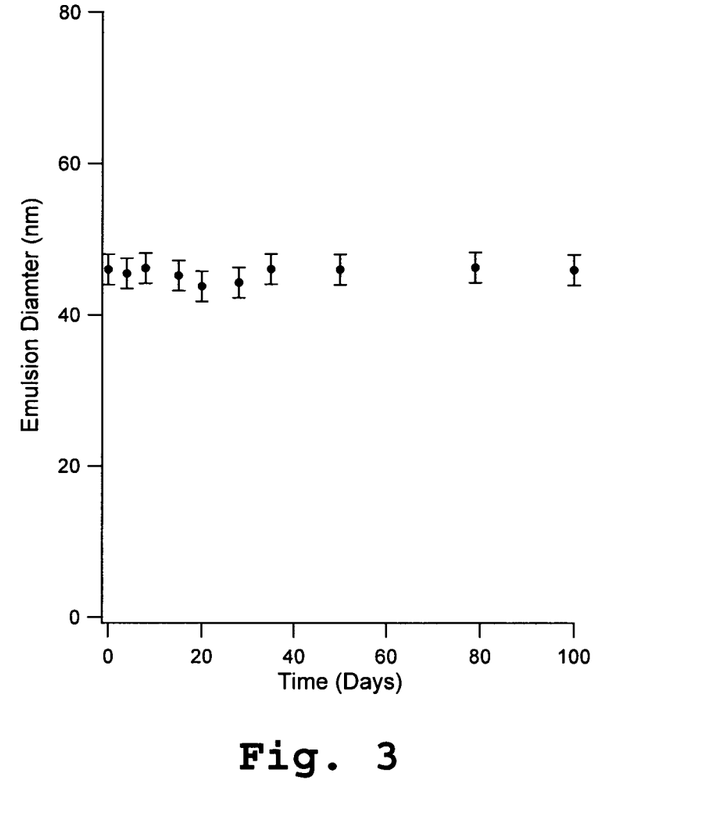
FIG. 3 is a graph showing the typical physical stability (change in average particle size over time during storage at 24° C.) of nanoemulsions outlined in examples 2-6.
Figure 4:
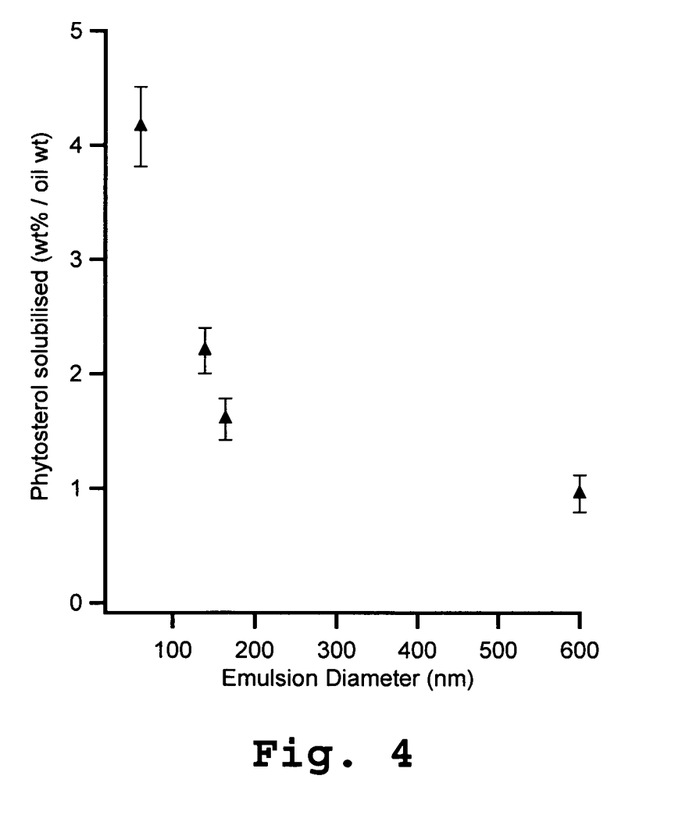
FIG. 4 is a graph comparing the ability of different sized canola oil emulsions to solubilise (dissolve) phytosterol. The emulsions were i) a conventional canola oil emulsion (600 nm diameter, 0.5 wt % polysorbate 80) ii) a high shear homogenised canola oil emulsion (160 nm diameter, 5.6 wt % polysorbate 80), iii) a microfluidized canola oil emulsion (130 nm diameter, 5.6 wt % polysorbate 80) iv) a canola oil nanoemulsion as outlined in Example 5 (50 nm diameter).
Figure 5:
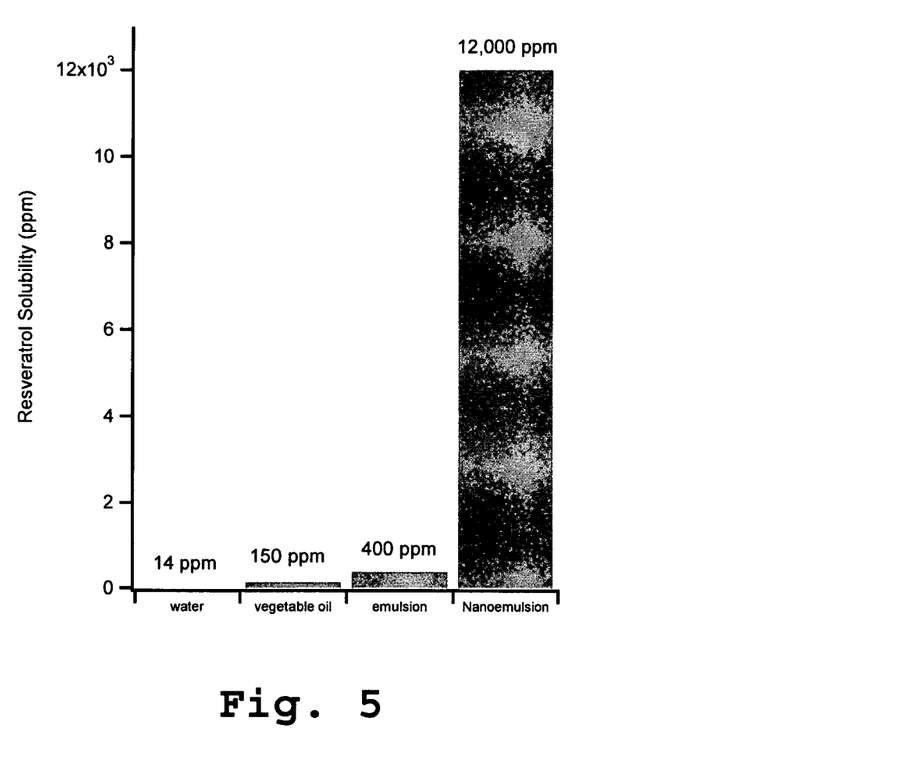
FIG. 5 is a graph comparing the solubility of resveratrol in i) water, ii) a long chain triglyceride, iii) a conventional long chain triglyceride emulsion (0.6 μm diameter, 0.5 wt % polysorbate 80) and iv) a edible nanoemulsion as outlined in example 11.

A nutritional supplement was created by dispersing powdered phytosterol with the oil phase ingredients (triglyceride oil, surfactant and/or co-surfactant) of examples 1-7 and heating above 100° C. This solution of phytosterol, oil and surfactant was then intermixed with 120 g of a 3 to 1 water to ethanol solution using a silverson rotor stator mixer at 12,000 rpm for 2 minutes to form a pre-emulsion. The pre-emulsion was then homogenised with a Microfluidizer™ at 1000 bar and 5 passes. The resulting nanoemulsion had an initial particle size of 45 nm and high optical clarity. HPLC analysis demonstrated that nanoemulsions prepared in this way were capable of dissolving to a much greater extent compared to oil, or a conventionally sized emulsion FIG. 3.

Example 13

β-Carotene Nanoemulsion

A nutritional supplement, or natural coloring agent was created by nanoemulsifying β-carotene that was dissolved/dispersed in a triglyceride oil. 23 g of a β-carotene loaded oil (e.g. Betatene 30% in olive oil) was thoroughly mixed with 8 grams of polyoxyethylene sorbitan mono-oleate (Tween 80) and 8 grams of Centromix E (lysolecithin). This oil/surfactant mixture was then intermixed into 120 g of a 3 to 1 water to ethanol solution with a silverson rotor stator mixer at 12,000 rpm for 2 minutes to form a pre-emulsion. The pre-emulsion was then homogenised with a Microfluidizer™ at 1000 bar and 5 passes. The resulting nanoemulsion had a particle size of 50 nm, had high optical clarity, a natural deep red colour, and did not change size over a 30 day storage period.

Example 14

Lutein Nanoemulsion

A nutritional supplement, or natural coloring agent was created by nanoemulsifying a mixture of lutein and lutein esters that were dissolved/dispersed in a triglyceride oil. 23 g of a lutein/lutein ester loaded oil (e.g. Xangold 15% in olive oil from Cognis) was thoroughly mixed with 8 grams of polyoxyethylene sorbitan mono-oleate (Tween 80) and 8 grams of Centromix E (lysolecithin). This oil/surfactant mixture was then intermixed into 120 g of a 3 to 1 water to ethanol solution with a silverson rotor stator mixer at 12,000 rpm for 2 minutes to form a pre-emulsion. The pre-emulsion was then homogenised with a Microfluidizer™ at 1000 bar and 5 passes. The resulting nanoemulsion had a particle size of 50 nm, had high optical clarity, a natural deep orange colour, and did not change size over a 30 day storage period.

Example 15

Retinyl Palmitate Nanoemulsion

A nutritional supplement, a natural colouring agent, or a cosmetic ingredient was created by nanoemulsifying a 1:1 mixture of; retinyl palmitate in oil and vegetable oil. Briefly, 12 g of a retinyl palmitate loaded sunflower oil (e.g. Vitamin A-Palmitate 1.0 Mio IU/G—BASF) and 12 g of sunflower oil, were thoroughly mixed with 8 grams of polyoxyethylene sorbitan mono-oleate (Tween 80) and 8 grams of Centromix E (lysolecithin). This oil/surfactant mixture was then intermixed into 120 g of a 3 to 1 water to ethanol solution with a silverson rotor stator mixer at 12,000 rpm for 2 minutes to form a pre-emulsion. The pre-emulsion was then homogenised with a Microfluidizer™ at 1000 bar and 5 passes. The resulting nanoemulsion had a particle size of 50 nm, had high optical clarity, a natural yellow colour, and did not change size over a 100 day storage period.

The above tuna oil examples can also act as a bioactive example as tuna oil is a bioactive.

In the subject specification except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It will be understood to persons skilled in the art of the invention that many modifications may be made without departing from the spirit and scope of the invention.

The invention claimed is:

1. An oil-in-water nanoemulsion which consists of up to 40 volume % of an oil phase comprising at least 50 volume % of a triglyceride having a fatty acid chain length of 12 carbon atoms or greater;
   a hydrophilic non-ionic surfactant having a hydrophilic-lipophilic balance (HLB) greater than 7; and
   an aqueous phase;
   optionally one or more additional oils;
   a co-solvent selected from the group consisting of methanol, ethanol, propanol and butanol, wherein the amount of col-solvent is 0.1 to 70 wt %;
   optionally a co-surfactant selected from a sorbitan fatty acid ester, phospholipid, sodium stearoyl lactylate and calcium stearoyl lactylate; and optionally an additive selected from a stabiliser, antioxidant, preservative, buffering agent, charge inducing agent, weighting agent and protein in which the oil droplets of the nanoemulsion have an intensity average size of less than 100 nm, the ratio of surfactant to oil is less than 1:1 and the nanoemulsion retains its structure upon dilution and/or acidification.

2. A nanoemulsion according to claim 1 in which the oil droplets have a diameter of 80 nm or less, 75 nm or less or 60 nm or less.

3. A nanoemulsion according to claim 1 in which the triglyceride is fish oil, cod liver oil, blubber, lard, tallow, schmaltz, and butter fat; vegetable origin such as canola oil, castor oil, cocoa butter, coconut oil, coffee seed oil, corn oil, cotton seed oil, evening primrose oil, grapeseed oil, flax seed oil, menhaden oil, mustard seed oil, olive oil, palm oil, palm kernel oil, peanut oil, poppy seed oil, rapeseed oil, rice bran oil, safflower oil, sesame oil, soybean oil, sunflower oil, palm kernel oil, hazelnut oil, sesame oil, wheat germ oil, vegetable oil, synthetic triglyceride, fractionated triglyceride, modified triglyceride, hydrogenated triglyceride, partially hydrogenated triglyceride or mixtures thereof.

4. A nanoemulsion according to claim 1 in which the ratio of triglyceride to additional oil is 1:0 to 1:1.

5. A nanoemulsion according to claim 1 in which the total amount of oil in the nanoemulsion comprising triglyceride and additional oil if present is 0.01 to 70 wt %, 0.01 to 50 wt % or 0.01 to 40 wt %.

6. A nanoemulsion according to claim 1 in which the hydrophilic non-ionic surfactant is selected from polysorbates, polyethylene glycol alkyl ethers, sugar esters, polyethoxylated fatty acids, polyoxyethylene-polyoxypropylene block co-polymers, polyethylene glycol alkyl phenol surfactants, citric acid esters of monoglycerides, polyglycerol esters, polyethoxylated fatty acid diesters, PEG-fatty acid mono and diesters, polyethylene glycol glycerol fatty acid esters and alcohol oil transesters or mixtures thereof.

7. A nanoemulsion according to claim 1 in which the amount of hydrophilic surfactant is 0.1 to 15 wt %, 1 to 10 wt % or 3 to 7 wt %.

8. A nanoemulsion according to claim 1 in which the amount of co-surfactant is 0.1 to 15 wt %.

9. A nanoemulsion according to claim 1 in which the co-surfactant is present in a ratio relative to the hydrophilic non-ionic surfactant of 0:1 to 2:1 0:1 to 1.3:1 or 0.5:1 to 1.3:1.

10. A nanoemulsion according to claim 1 in which balance of water is 50 to 100 wt %, 40 to 99.99 wt % or 30 to 99.90 wt %.

11. A delivery vehicle for an active component comprising the nanoemulsion according to claim 1.

12. A formulation comprising the nanoemulsion according to claim 1, and an active component.

13. A formulation according to claim 12 in which the active component is selected from food supplements, food additives, aromas, aromatic oils, colours, flavours, sweeteners, cosmetics, pharmaceuticals, nutraceuticals, phytochemicals, vitamins, essential polyunsaturated fatty acids, plant extracts, agrichemicals, textiles, polymers and chemicals.

* * * * *